United States Patent [19]
Gerlacher et al.

[11] Patent Number: 5,087,123
[45] Date of Patent: * Feb. 11, 1992

[54] ATOMIC EMISSION SPECTROMETER WITH BACKGROUND COMPENSATION

[75] Inventors: Edgar Gerlacher, Konstanz; Carl G. Dencks, Owingen; Uwe Gunther, Owingen; Gunther Rodel, Owingen, all of Fed. Rep. of Germany

[73] Assignee: Bodenseewerk Perkin Elmer GmbH, Uberlingen, Fed. Rep. of Germany

[*] Notice: The portion of the term of this patent subsequent to Mar. 26, 2008 has been disclaimed.

[21] Appl. No.: 526,779

[22] Filed: May 17, 1990

Related U.S. Application Data

[63] Continuation of Ser. No. 335,065, Apr. 7, 1989, abandoned.

Foreign Application Priority Data

Apr. 9, 1988 [DE] Fed. Rep. of Germany ....... 3811923

[51] Int. Cl.⁵ .............. G01J 3/36; G01J 3/28
[52] U.S. Cl. .................... 356/307; 356/328
[58] Field of Search .......... 356/328, 326, 311, 307, 356/305, 316

[56] References Cited

U.S. PATENT DOCUMENTS

| | | | |
|---|---|---|---|
| 4,158,505 | 6/1979 | Mathisen et al. ................ | 356/308 |
| 4,591,267 | 5/1986 | Demers et al. ................... | 356/316 |
| 4,820,048 | 4/1989 | Barnard .......................... | 356/328 |
| 5,002,390 | 3/1991 | Gerlacher et al. ............... | 356/307 |

OTHER PUBLICATIONS

Weekly et al., "A Versatile Electronic Computer for Photoelectric Spectrochemical Analysis," Applied Spectroscopy, vol. 18, #1, 1964, p. 22.

*Primary Examiner*—F. L. Evans
*Assistant Examiner*—K. P. Hantis
*Attorney, Agent, or Firm*—Edwin T. Grimes

[57] ABSTRACT

A method of and a device for multi-element measurement of elements in a sample with correction for background emission. The method starts with atomizing a sample and then exciting the transformed atoms to emit light containing characteristic spectral lines for each element, followed by generating a spectrum of spectral lines characteristic of the elements, followed by measuring the intensity of selected spectral lines falling within a predetermined measuring range without changing their intensity. The next steps are sensing the background emission adjacent the selected spectral lines simultaneously with measuring the intensity of selected spectral lines and determining the concentration of each element from the measured intensity of the corresponding spectral line and sensed background emission.

18 Claims, 2 Drawing Sheets

ATOMIC EMISSION SPECTROMETER WITH BACKGROUND COMPENSATION

This application is a continuation of application Ser. No. 07/335,065 filed Apr. 7, 1989, now abandoned.

BACKGROUND AND SUMMARY OF THE INVENTION

This invention relates to atomic emission spectroscopy and more particularly to a background compensation apparatus and technique for an atomic emission spectrometer for multi-element measurement of elements in a sample.

Atomic absorption spectroscopy (hereinafter "AAS") is a known procedure for measuring the concentration of a certain element in a sample. AAS utilizes the fact that atoms absorb light at certain wavelengths characteristic of the particular element. Atoms emit light in the form of a line spectrum when they are excited and the line spectrum is characteristic of the respective element. Correspondingly, the atoms absorb light only at the wavelengths of this line spectrum.

In AAS, an atomizing device in the form of a flame burner or a graphite furnace for electrothermal atomization is utilized to generate an atomic vapor of the sample in which the atoms of the sample are present in their atomic state. A measuring light beam is normally generated by a hollow cathode lamp and consists of light with the line spectrum of the looked-for element. This measuring light beam is passed through the atomic vapor and is subjected to absorption indicative of the amount of the looked-for element in the sample. The other components of the sample, at least theoretically, do not influence the measuring light beam because their absorption lines do not coincide with the line spectrum of the measuring light beam. The measuring light beam impinges on a photoelectric detector and the concentration of the looked-for element is determined from the detector signal after suitable processing and calibration.

In addition to the specific absorption caused by the atoms of the looked-for element (i.e., atomic absorption), there normally occurs a non-specific absorption referred to as background absorption which is caused by solid particles or molecules in the path of the measuring light beam. This background absorption can have the magnitude of the atomic absorption or can even be larger. Therefore, background absorption has to be determined and taken into consideration with highly sensitive measurements. In AAS, background absorption correction can be achieved by alternating between the line emitting light source and a light source emitting a continuum or by using the Zeeman effect in which either the emitted spectral lines of the light source or the absorption lines of the sample are shifted for the background measurement. These methods are quite expensive and require an additional light source or a strong electromagnet which is arranged to be energized or de-energized.

A disadvantage of AAS is that the elements can only be determined one by one, i.e., one after the other.

Therefore, another known analytical procedure is to measure the emission of a sample rather than the absorption, i.e., atomic emission spectroscopy, which allows multi-element measurement.

In atomic emission spectroscopy, plasma burners are often used as the atomization and excitation device. In plasma burners, an emerging inert gas is inductively transformed to a plasma of high temperature and the sample is led into this plasma. In another prior art atomization and excitation device, a sample is electrothermally dried and ashed in a graphite furnace similar to the graphite tubes used in AAS. The graphite furnace is then evacuated and an inert gas is introduced. Subsequently, an electrothermal atomization of the sample is effected. A gas discharge is caused in the mixture of inert gas and sample vapor by an anode such that the graphite tube operates as a hollow cathode lamp. The graphite tube serves as a hollow cathode.

A spectrum of the emitted light is generated by means of a polychromator. It is known to scan such a spectrum by means of a series detector or "detector array" consisting of a plurality of photodetectors. The entire spectrum is detected which results in a great amount of data and the signal processing is correspondingly complex.

A polychromator is known in which a dispersion is effected in high order in a first direction by an echelle grating. The different orders overlap and a dispersion is effected in a second direction perpendicular to the first direction by a dispersion prism whereby the different orders are separated. This results in a two-dimensional spectrum with very high resolution in a focal plane.

In the prior art polychromator, a mask with apertures at the location of the spectral lines of the spectrum which are characteristic of a certain element is arranged in the focal plane. These apertures are arranged to accommodate light pipes, each of which is guided to an associated photomultiplier. The number of available photomultipliers and thus the number of elements which can be analyzed simultaneously is therefore necessarily limited due to cost considerations. One mirror of the polychromator is movable through small angles to compensate for the background emission which occurs in a similar way as the background absorption described above. The generated spectrum is periodically shifted relative to the light pipes such that the light pipes detect the light outside the spectral lines.

It is an object of the present invention to provide a new and improved atomic emission spectrometer with background emission compensation.

Another object of the invention is to provide such an atomic emission spectrometer for multi-element measurement which attains simultaneous measurement of a relatively large number of elements with simultaneous measurement and correction of background emission.

Another object of the invention is to provide a background emission correction device and technique for an atomic emission spectrometer which is economical.

Other objects will be in part obvious and in part pointed out more in detail hereinafter.

Accordingly, it has been found that the foregoing and related advantages are attained in an atomic emission spectrometer for multi-element measurement which includes an apparatus to atomize a sample and excite the atoms to emit characteristic spectral lines, a dispersion assembly to generate a spectrum of characteristic spectral lines in a focal plane, a first photodetector assembly for simultaneously sensing the intensity of spectral lines of a plurality of elements, a second photodetector assembly for sensing background emission outside the spectral lines sensed by the first photodetector assembly, and processing circuit means for determining the concentrations of the plurality of elements with correction for background emission.

The second photodetector assembly has a plurality of semiconductor photodetectors disposed for sensing background emission adjacent the spectral lines for generating a correction signal which corresponds to the background emission at the wavelengths of the spectral lines measured. The first photodetector assembly may comprise a plurality of semiconductor photodetectors positioned for simultaneously sensing a plurality of spectral lines for each element of the sample to be tested and an evaluation circuit selects the semiconductor photodetectors sensing the spectral line for each element which has an intensity optimally within the sensing range of the respective semiconductor photodetector. The measured intensity is corrected with the background emission correction signal with the concentrations of the elements being determined from the corrected intensities.

DESCRIPTION OF THE PREFERRED EMBODIMENT

Figure 1:
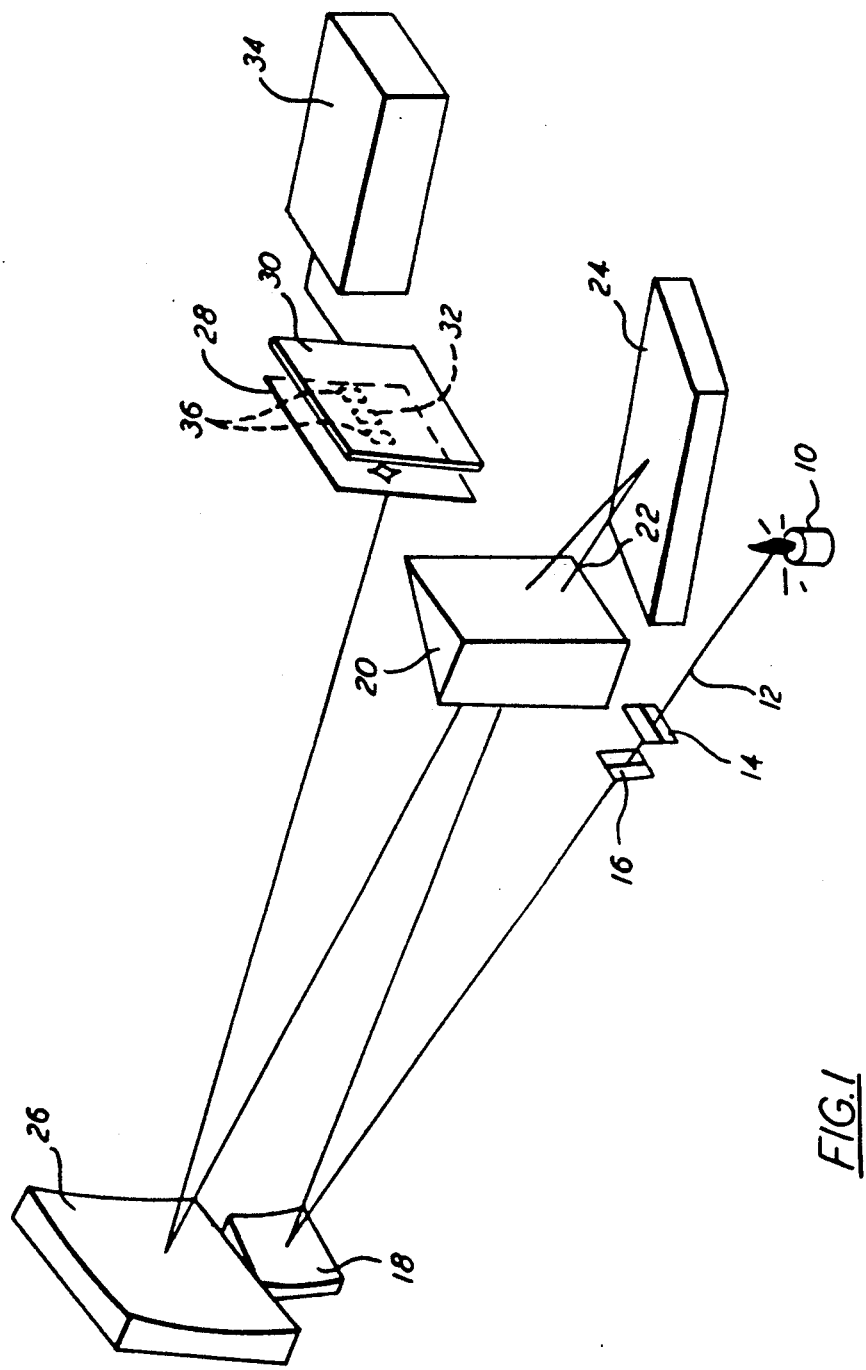
FIG. 1 is a schematic perspective view of an atomic emission spectrometer for multi-element measurement with semiconductor photodetectors.

Although specific forms of the present invention have been selected for illustration in the drawings, and the following description is drawn in specific terms for the purpose of describing these forms of the invention, the description is not intended to limit the scope of the invention which is defined in the appended claims.

Referring to FIG. 1, the numeral 10 designates an atomization and excitation device which is illustrated here as a plasma burner. Alternately, a hollow cathode lamp such as disclosed in German patent C2-30,13,354 may be used which comprises a graphite tube for electrothermal drying, ashing and atomization of the sample and an anode. Such a hollow cathode lamp is evacuated after ashing and is filled with inert gas. After atomization, a gas discharge is generated during which the graphite tube assumes the function of a hollow cathode.

A light beam 12 originates from the atomization and excitation device 10 and is formed by light with line spectra of the different elements contained in the sample. These line spectra are emitted due to the excitation of the atoms of the elements contained in the sample. The line spectra are characteristic of the respective element and each comprises several spectral lines. The intensities of the spectral lines are proportional to the amount or the concentration of the element in the sample. The spectral lines of a line spectrum characteristic of a certain element have different intensities. Each line spectrum has spectral lines with a relatively high intensity and other weaker spectral lines with a relatively low intensity.

The light beam 12 is limited by a main slit 14 extending horizontally in FIG. 1 and a transverse slit 16 extending perpendicular thereto. The light beam 12 is collimated by a collimator mirror 18 and is passed through a dispersion prism 20. The light beam 22, once spectrally dispersed by the dispersion prism 20, is incident at a large angle of incidence on the echelle grating 24, i.e., with a small angle between the beam and the grating. The echelle grating accomplishes a spectral dispersion of the light beam 22 by diffraction in a direction perpendicular to that in which the dispersion was accomplished by the dispersion prism 20, i.e., in a substantially vertical plane in FIG. 1. This diffraction is observed in high order. A very large spectral dispersion is effected but with a large overlap of the different orders. The diffracted light passes through the dispersion prism 20 again and is collected by a camera mirror 26 in a focal plane 28.

A highly resolved spectrum with the lines of the single elements is generated in the focal plane 28. The different orders of the echelle grating 24 are separated by the dispersion prism 20 and are located in the spectrum side by side. The individual lines appear as light points.

Figure 2:
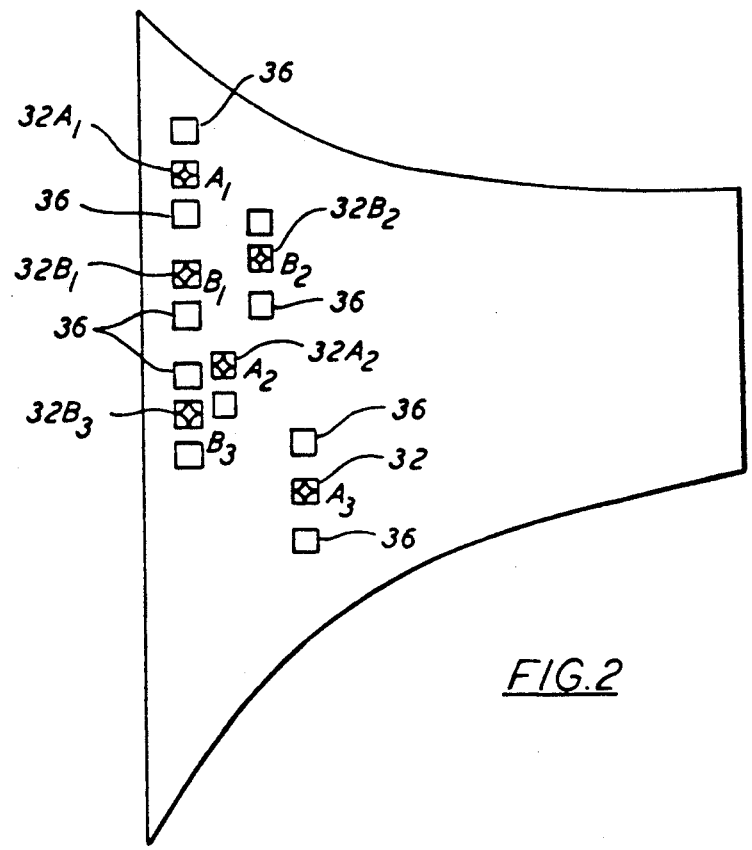
FIG. 2 is a diagrammatic view of a spectrum as obtained in the focal plane of the atomic emission spectrometer of FIG. 1.

FIG. 2 is a schematical illustration of the arrangement of the spectral lines in the spectrum. For clarity, only spectral lines for two elements are indicated, which are designated by "A" and "B".

Figure 3:
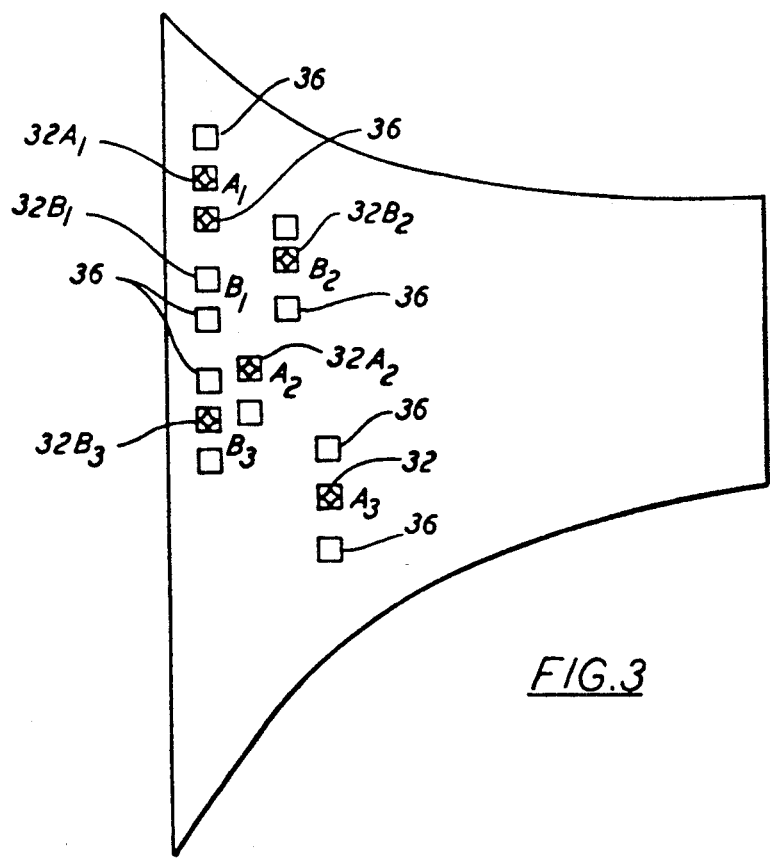
FIG. 3 is a diagrammatic view of the position of semiconductor photodetectors relative to the spectral lines.

A detector carrier 30 is arranged in the focal plane. Semiconductor photodetectors 32 are arranged on this detector carrier, each at the location of an associated spectral line. As can be seen in FIG. 3, one semiconductor photodetector 32 each are arranged at the location of several spectral lines of each element. In FIG. 3, semiconductor photodetectors 32A1, 32A2, and 32A3 are arranged at the locations of the spectral lines A1, A2 and A3, respectively, of the element A. Correspondingly, semiconductor photodetectors 32B1, 32B2, and 32B3 are arranged at the locations of the spectral lines B1, B2 and B3. The spectral line A1 is the main line of the element A and has the highest intensity compared to the intensities of the other spectral lines of the element A. The second spectral line A2 has an intensity which is lower by some orders of magnitude than the intensity of the main line A1. The third spectral line A3 is even substantially weaker than the second spectral line A2. The relations of the spectral lines of element B are similar.

The semiconductor photodetectors 32 are connected to an evaluating circuit 34 which is indicated by a block in FIG. 1. The evaluating circuit 34 checks each semiconductor photodetector 32 for whether its signal lies within the measuring range of the semiconductor photodetector or whether the semiconductor photodetector is saturated by the intensity of the associated spectral line, A1, for example. The signal of such a semiconductor photodetector (32A1) is not processed further. Then the same check of the semiconductor photodetector 32A2 and, if required, also of the semiconductor photodetector 32A3 is carried out. If the signal of a semiconductor photodetector lies in its measuring range, the signal is processed further with a factor which corresponds to the ratio of the intensities of the respective spectral line and the reference line, spectral line A1, for example.

Thereby, the ratios of the intensities of different spectral lines used are superposed to the dynamic range of the semiconductor photodetector such that a sufficiently large dynamic range is obtained. The selection of the signal to be processed can be made automatically by the evaluating circuit 34. It is not necessary to adjust the different photodetectors prior to the actual measurement as with the prior art photomultipliers.

Thus, the detector assembly comprises a plurality of semiconductor photodetectors 32, each of which is exposed to one of the characteristic lines. A plurality of semiconductors is provided for each element to be measured with the semiconductor photodetectors being exposed to different spectral lines of different intensities of the light spectrum emitted by the atoms of the element. The evaluating circuit is adapted to select, for measuring each element, one semiconductor photodetector for which the intensity of the associated spectral line lies in a part of the measuring range of the semiconductor photodetector which is as favorable as possible.

Additional semiconductor photodetectors 36 are provided to correct for background, i.e., background emission. The semiconductor photodetectors 36 are arranged outside the spectral lines, preferably close thereto, and provide the course of the background emission. A value of the background emission at the location of the spectral lines can be obtained from the signals of the semiconductor photodetectors 36. The measured intensity of the spectral lines can be corrected based upon this background value in order to obtain an exact measuring value of the concentration of the respective element in the sample.

Accordingly, the plurality of semiconductor photodetectors 32 senses the characteristic spectral lines and the additional semiconductor photodetectors 36 are disposed closely adjacent the spectral lines so as to sense background emission. The signal evaluation circuit 34 selects a photodetector 32 (as described above) for each element and generates from the signals of photodetectors 36 a correction signal which corresponds to the background emission at the wavelengths of the spectral lines measured by the photodetectors 32. The signal evaluation circuit 34 makes a background emission correction of the measured intensities of the spectral lines and the concentrations of the elements are determined from the corrected intensities.

The semiconductor photodetectors can be mounted on a carrier one by one in a two-dimensional arrangement. The semiconductor photodetectors can also be arranged in an integral unit. The semiconductor photodetectors are of such small dimensions and are relatively inexpensive such that a great number of sample elements and the background emission value can be simultaneously measured in the way described with a plurality of such semiconductor photodetectors being provided for each element. However, it is not necessary to detect each wavelength virtually continuously. Thereby, the expenditure for the signal processing is kept within acceptable limits. It is also possible to scan and process the signals of all semiconductor photodetectors virtually simultaneously with reasonable expenditure such that the concentrations of the different elements are associated with the same point in time.

Accordingly, small and relatively inexpensive photodetectors can be used and the technical expenditure thereby becomes smaller. Using several of such semiconductor photodetectors for each individual element permits, on one hand, the required dynamic range to be achieved by such semiconductor photodetectors. On the other hand, the use of a plurality of photodetectors for each element becomes economically possible because of the use of the (inexpensive) semiconductor photodetectors.

Furthermore, the use of semiconductor photodetectors offers the possibility to generate a background signal in the focal plane by additional semiconductor photodetectors at other suitable locations of the generated spectrum to compensate the measuring signal with respect to background.

As can be seen, an atomic emission spectrometer for multi-element measurement has been described which attains simultaneous measurement of a relatively large number of elements with simultaneous measurement and correction for background emission.

As will be apparent to persons skilled in the art, various modifications and adaptations of the structure above described will become readily apparent without departure from the spirit and scope of the invention, the scope of which is defined in the appended claims.

What is claimed is:

1. An atomic emission spectrometer for multi-element measurement of elements in a sample comprising
   means for atomizing a sample and for exciting atoms to emit light with characteristic spectral lines of elements contained in the sample,
   dispersing means for generating a spectrum of characteristic spectral lines of the emitted light in a focal plane,
   first photodetector means for simultaneously sensing spectral lines of multiple elements in the sample for processing to determine concentration,
   second photodetector means for sensing background emission outside the spectral lines sensed by said first detector means for processing to determine background emission correction,
   measuring range circuit means, associated with said first photodetector means, for determining whether said first photodetector means senses spectral lines within a measuring range of said first photodetector means and selecting for processing only spectral lines sensed by said first photodetector means within the measuring range without changing the intensity of any of the spectral lines at said first photodetector means, and
   processing circuit means for determining concentration of the multiple elements in the sample with correction for background emission.

2. The device of claim 1 wherein said second photodetector means is disposed for sensing background emission closely adjacent said spectral lines.

3. The device of claim 1 wherein said second photodetector means is positioned within said focal plane for sensing background emission closely adjacent said spectral lines.

4. The device of claim 1 wherein said second photodetector means comprises a plurality of semiconductor photodetectors disposed for sensing background emission outside the spectral lines of the multiple elements to be determined.

5. The device of claim 4 wherein said second photodetector means comprises a carrier mounting said plurality of semiconductor photodetectors, said semiconductor photodetectors being mounted in said focal plane and disposed for sensing background emission closely adjacent the spectral lines of the multiple elements to be determined.

6. An atomic emission spectrometer for multi-element measurement of elements in a sample comprising
   means for atomizing a sample and for exciting atoms to emit light with characteristic spectral lines of elements contained in the sample,
   dispersing means for generating a spectrum of characteristic spectral lines of the emitted light in a focal plane,
   first photodetector means for simultaneously sensing the intensity of spectral lines of a plurality of elements, said first photodetector means comprising a plurality of first semiconductor photodetectors disposed for simultaneously sensing spectral lines of a plurality of elements in said generated spectrum, second photodetector means for sensing background emission outside the spectral lines sensed by said first photodetector means, said second photodetector means comprising a plurality of second semiconductor photodetectors disposed for sensing background emission outside said spectral lines, measuring range circuit means, associated with said first photodetector means, for determining whether said first photodetector means senses spectral lines within a measuring range of said first photodetector means and selecting for processing only spectral lines sensed by said first photodetector means within the measuring range without changing the intensity of any of the spectral lines at said first photodetector means, and processing circuit means for determining the concentrations of the plurality of elements with correction for background emission, said processing circuit means comprising signal evaluation circuit means for generating a correction signal corresponding to background emission at the wavelengths of the measured spectral lines.

7. The device of claim 6 wherein
said plurality of first semiconductor photodetectors are disposed so that spectral lines of each element to be tested are each sensed by a said first semiconductor photodetector, and said plurality of second semiconductor photodetectors are disposed for sensing background emission adjacent the spectral lines sensed by said first semiconductor photodetectors.

8. The device of claim 7 wherein said signal evaluation circuit means comprises selection circuit means for selecting a first semiconductor photodetector for each element such that the selected first semiconductor photodetector is measuring intensity of a spectral line having an intensity optimally within the sensing range of said first semiconductor photodetector, said signal evaluation circuit means correcting said measured intensities with said correction signal.

9. The device of claim 7 wherein said second semiconductor photodetectors are positioned substantially within said focal plane.

10. The device of claim 7 which comprises a carrier mounting said first and second semiconductor photodetectors substantially within said focal plane.

11. The device of claim 7 wherein said second semiconductor photodetectors are sensing background emission closely adjacent said spectral lines.

12. The device of claim 6 which comprises a carrier mounting said first and second semiconductor photodetectors substantially within said focal plane.

13. An atomic emission spectroscopy method of multi-element measurement of elements in a sample with correction for background emission comprising
atomizing a sample so that the elements of the sample are transformed into an atomic state,
exciting the transformed atoms to emit light containing characteristic spectral lines for each element,
generating a spectrum of spectral lines characteristic of said elements from said emitted light,
measuring the intensity of selected spectral lines falling within a predetermined measuring range without changing their intensity,
sensing background emission adjacent the selected spectral lines simultaneously with measuring the intensity of selected spectral lines, and
determining the concentration of each element from the measured intensity of the corresponding spectral line and sensed background emission.

14. The method of claim 13 wherein the step of sensing the background emission comprises sensing the background emission with a plurality of semiconductor photodetectors closely adjacent the selected spectral lines.

15. The method of claim 14 wherein the spectrum is generated in a focal plane and the background emission is sensed substantially in the focal plane.

16. The method of claim 15 wherein the step of measuring the intensity of selected spectral lines comprises
sensing a predetermined number of said spectral lines for each element with a plurality of semiconductor photodetectors having an optimal operating range,
evaluating said photodetectors to determine for each element the particular photodetector sensing the corresponding spectral line with an intensity within said operating range, and
measuring the intensity of the spectral line for each element within said operating range.

17. An atomic emission spectrometer for multi-element measurement of elements in a sample comprising:
means for atomizing a sample and for exciting atoms to emit light with characteristic spectral lines of elements contained in the sample,
dispersing means for generating a spectrum of characteristic spectral lines of the emitted light in a focal plane,
first photodetector means for simultaneously sensing spectral lines of multiple elements in the sample for processing to determine concentration,
measuring range circuit means, associated with said first photodetector means, for determining whether said first photodetector means senses spectral lines within a measuring range of said first photodetector means and processing only spectral lines sensed by said first photodetector means within the measuring range;
evaluating circuit means, associated with said measuring range circuit means, for selecting the one spectral line that best fits within the measuring range;
second photodetector means for sensing background emission outside the spectral lines sensed by said first detector means for processing to determine background emission correction; and
processing circuit means for determining concentration of the multiple elements in the sample with correction for background emission.

18. An atomic emission spectrometer for multi-element measurement of elements in a sample comprising:
means for atomizing a sample and for exciting atoms to emit light with characteristic spectral lines of elements contained in the sample;
dispersing means for generating a spectrum of characteristic spectral lines of the emitted light in a focal plane;
a plurality of first photodetectors arranged at the location of several spectral lines of each element;
evaluating circuit means, associated with each said plurality of first photodetectors, for evaluating the intensity of a spectral line at one location of several spectral lines of each element and for selecting one spectral line that best fits in a measuring range of one of said plurality of first photodetectors at the one location;

factor means, associated with said evaluation circuit means, for applying a factor to said one spectral line which corresponds to the ratio of the intensities of said one spectral line for each element and a spectral line having the highest intensity compared to the intensity of the other spectral lines for each element;

second photodetector means for sensing background emission outside the spectral lines sensed by said first detector means for processing to determine background emission correction; and processing circuit means for determining concentration of the multiple elements in the sample with correction for background emission.

* * * * *